(12) United States Patent
Zhang et al.

(10) Patent No.: US 8,494,631 B2
(45) Date of Patent: Jul. 23, 2013

(54) SYSTEM AND METHOD FOR PROFILING A PATIENTS HEMODYNAMIC RESPONSE BASED ON HEART SOUNDS

(75) Inventors: Xusheng Zhang, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 13/222,176

(22) Filed: Aug. 31, 2011

(65) Prior Publication Data

US 2013/0053716 A1 Feb. 28, 2013

(51) Int. Cl.
*A61N 1/00* (2006.01)

(52) U.S. Cl.
USPC .......................................................... 607/18

(58) Field of Classification Search
USPC ...................................................... 607/4–28
See application file for complete search history.

(56) References Cited

U.S. PATENT DOCUMENTS

| | | | |
|---|---|---|---|
| 4,546,777 A | 10/1985 | Groch | |
| 5,554,177 A | 9/1996 | Kieval | |
| 5,683,432 A | 11/1997 | Goedeke | |
| 6,418,346 B1 | 7/2002 | Nelson | |
| 6,442,433 B1 | 8/2002 | Linberg | |
| 6,477,406 B1 * | 11/2002 | Turcott | 600/518 |
| 6,480,745 B2 | 11/2002 | Nelson | |
| 6,527,729 B1 | 3/2003 | Turcott | |
| 6,599,250 B2 | 7/2003 | Webb | |
| 6,869,404 B2 | 3/2005 | Schulhauser | |
| 6,871,088 B2 * | 3/2005 | Chinchoy | 600/510 |
| 7,035,684 B2 | 4/2006 | Lee | |
| 7,548,784 B2 | 6/2009 | Chinchoy | |
| 7,559,900 B2 | 7/2009 | Gillberg | |
| 7,585,279 B2 | 9/2009 | Carlson | |
| 7,682,316 B2 | 3/2010 | Anderson | |
| 2002/0161307 A1 | 10/2002 | Yu | |
| 2004/0167417 A1 | 8/2004 | Schulhauser | |
| 2008/0103406 A1 | 5/2008 | Kameli | |
| 2008/0243202 A1 | 10/2008 | Patangay | |
| 2011/0009760 A1 | 1/2011 | Zhang | |

OTHER PUBLICATIONS

Van Bommel et al. Critical appraisal of the use of cardiac resynchronization therapy beyond current guidelines, J Am Coll Cardiol 2010, 56 (10), 754-762.
Auricchio A, et al. Effect of pacing chamber and atrioventricular delay on acute systolic function of paced patients with congestive heart failure. Circulation 1999; 99; 2993-3001.
Packer, M: Proposal for a New Clinical End Point to Evaluate the Efficacy of Drugs and Devices in the Treatment of Chronic Heart Failure; Journal of Cardiac Failure 2001;7(2):176-182.

\* cited by examiner

*Primary Examiner* — Scott Getzow
(74) *Attorney, Agent, or Firm* — Michael C. Soldner

(57) ABSTRACT

A medical device system includes electrodes for delivering cardiac pacing pulses to a patient's heart, a cardiac sensing module coupled to the electrodes and a cardiac pacing module coupled to the electrodes for generating cardiac pacing pulses. An acoustical sensor is used for obtaining heart sound signals. The system includes a processor that is configured to establish multiple conditions during which heart sound signals are received. The processor derives heart sound signal parameters from the heart sound signals and determines a heart sound profile comprising a trend of each of the heart sound signal parameters with respect to the multiple established conditions.

23 Claims, 10 Drawing Sheets

US 8,494,631 B2

SYSTEM AND METHOD FOR PROFILING A PATIENTS HEMODYNAMIC RESPONSE BASED ON HEART SOUNDS

FIELD OF THE DISCLOSURE

The disclosure relates to a medical device system and associated method for profiling a patient's hemodynamic response based on heart sounds.

BACKGROUND

Cardiac resynchronization therapy (CRT) is one therapy used to treat heart failure (HF) patients. During CRT, pacing pulses are delivered to one or more heart chambers to restore synchrony of the heart chambers. Guidelines for selecting patients for CRT have been established, e.g. New York Heart Association (NYHA) classification III to IV, left ventricular ejection fraction (LVEF) 35% or less, and a wide QRS complex of 120 ms or more. Despite these guidelines, it may be possible that not all patients benefit from CRT. Some patients, referred to as "responders," present clinical improvement, e.g. improvement in NYHA class or other clinical measures, and may present improvement in a cardiac function measurement, e.g. decrease in left ventricular end systolic volume (LVESV), in response to CRT therapy. Other patients selected for CRT, referred to as "non-responders", may present no improvement, clinically or hemodynamically. Clinical end points for evaluating the efficacy of CRT are still evolving. Because of the varied response to CRT between patients meeting current therapy selection guidelines, patient selection for CRT and subsequent follow-up and evaluation continues to be challenging to clinicians.

Once a patient is selected for a pacing therapy, optimizing timing of pacing parameters is important in achieving therapeutic benefit of the pacing therapy, or at least preventing unintentional deleterious hemodynamic effects of the pacing therapy. Pacing timing control parameters include the atrial-ventricular (AV) interval used during single chamber ventricular pacing, during dual chamber (atrial and ventricular) pacing, and multi-chamber pacing, and the intra-ventricular (VV) interval used during biventricular or multichamber pacing. The AV interval is a pacing control time interval started upon sensing an atrial event (P-wave) or delivering an atrial pacing pulse. Upon expiration of the AV interval, the pacing device delivers a ventricular pacing pulse if an intrinsic ventricular event (R-wave) is not sensed during the AV interval. Similarly, the VV interval is used to control the timing of a ventricular pacing pulse following a programmed VV interval after a paced or sensed R-wave occurring in the other ventricular chamber.

Echocardiography continues to be a "gold standard" for optimizing pacing timing parameters. Echocardiography, however, tends to be a costly and time-consuming procedure which requires specially trained sonographers to perform. Other methods for monitoring hemodynamic performance of the heart typically require relatively more invasive techniques such as cardiac catheterization for measuring left ventricular (LV) pressure, cardiac output or other standard hemodynamic measurements. As such, the frequency that such techniques can be used to determine the best pacing parameters for an individual patient are limited due to time, cost, burden on the patient, and/or known inherent risks associated with invasive methods. It would be desirable for a clinician to know with a relatively high certainty beforehand whether a patient will be responsive to a given therapy and how best to manage the therapy to avoid or minimize costly, time-consuming and invasive procedures.

Other methods proposed for selecting CRT patients and optimizing CRT therapy include measuring the QRS width measured from ECG signals and performing adjustments to cause a narrowing of the QRS width. This technique assumes that a wider QRS width indicates greater ventricular dyssynchrony and a narrowing of the QRS width will be associated with improved ventricular synchrony. In a significant number of patients, however, electrical dyssynchrony and mechanical synchrony do not strongly correlate. As such, patient selection and optimization based on QRS width may have limited utility.

A need remains, therefore, for a medical device system and associated method for predicting a patient hemodynamic response to a therapy and for enabling identification of patients that can potentially benefit from a cardiac therapy. Furthermore, a technique that provides an indication of how a therapy can be tailored to a given patient to maximize patient benefit and minimize unneeded procedures is desirable.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
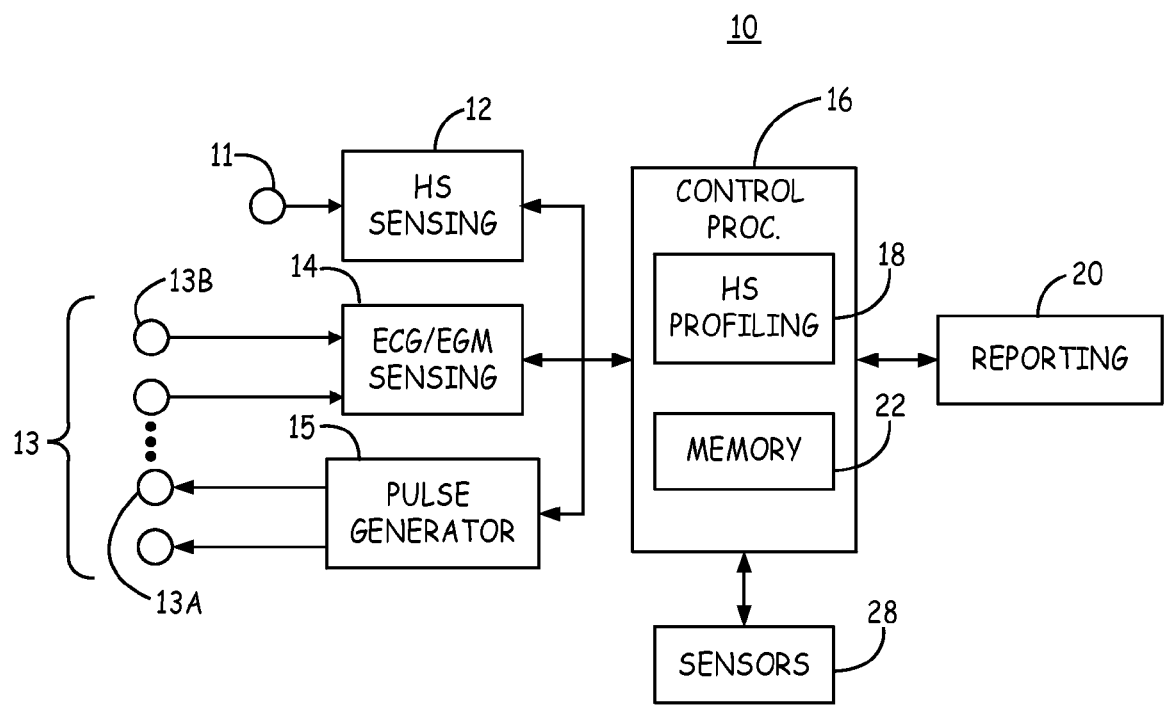
FIG. 1 is a functional block diagram of a system for profiling a patient's hemodynamic response to a pacing algorithm based on heart sounds according to one embodiment.

FIG. 1 is a functional block diagram of a system 10 for profiling a patient's hemodynamic response to a pacing algorithm according to one embodiment. The patient's hemodynamic response profile is based on heart sounds. The pacing algorithm is performed to obtain the patient's hemodynamic response profile for use as a patient selection tool for identifying patients having a profile that is predictive of a positive response to a cardiac pacing therapy. System 10 includes a heart sound (HS) sensing module 12 coupled to an acoustical sensor 11 responsive to heart sounds. System 10 further includes cardiac signal sensing circuitry 14 and pacing pulse generator 15 coupled to electrodes 13, a control processor 16 and a reporting module 20. Acoustical sensor 11 is provided for sensing heart sounds and HS sensing module 12 provides HS signals to control processor 16 for generating a patient hemodynamic profile based on heart sounds.

Physicians are particularly familiar with evaluating heart sounds as part of a basic physical examination, and a stethoscope is a standard component in a physician's diagnostic tool box. Using a HS sensor as a component of a medical device system for automatically generating patient hemodynamic profiles will enable clinicians to quickly obtain a predicted patient response to a cardiac therapy and may provide an indication of how the therapy should be managed for the particular patient as will be further described herein.

Clinicians typically refer to four heart sounds, S1, S2, S3 and S4. As will be described herein, the amplitudes and/or relative time intervals of one or more of the S1 through S4 heart sounds may be useful in generating patient hemodynamic profiles. The first heart sound, S1, corresponds to the start of ventricular systole. Ventricular systole begins when an action potential conducts through the atrioventricular node (AV node) and quickly depolarizes the ventricular myocardium. This event is distinguished by the QRS complex on the ECG. As the ventricles contract, pressure in the ventricles begins to rise, causing abrupt closure of the mitral and tricuspid valves between the ventricles and atria as ventricular pressure exceeds atrial pressure. This valve closure generates S1. S1 generally has a duration of about 150 ms and a frequency bandwidth on the order of 20 to 250 Hz. The amplitude of S1 may provide a surrogate measurement of LV contractility, which is conventionally measured as a maximum dP/dt from an intra-ventricular pressure signal.

Left ventricular pressure (LVP) rises dramatically following the QRS complex of the ECG and closure of the mitral valve and continues to build during ventricular systole until the aortic and pulmonary valves open, ejecting blood into the aorta and pulmonary artery. Ventricular contraction continues to cause blood pressure to rise in the ventricles and the aorta and pulmonary artery during the ejection phase. As the contraction diminishes, blood pressure decreases until the aortic and pulmonary valves close. The second heart sound, S2, is generated by the closure of the aortic and pulmonary valves, near the end of ventricular systole and start of ventricular diastole. S2 is therefore correlated to diastolic pressure in the aorta and the pulmonary artery. S2 generally has a duration of about 120 ms and a frequency bandwidth on the order of 25 Hz to 350 Hz.

One method for optimizing the AV interval during CRT involves pulsed Doppler echocardiography and adjusting the AV interval to increase the separation of the A wave and the E wave without A wave truncation. The E (early) wave and the A (atrial) wave represent the measurement of blood flow velocity across the mitral valve, with the E-wave occurring during passive filling of the ventricle and the A-wave occurring during active ventricular filling due to atrial systole. Greater separation of the E-wave and A-wave is thought to improve ventricular filling, when truncation of the A-wave due to onset of ventricular contraction is avoided. The occurrence of a sudden change in the timing of S2 relative to a ventricular sensed event (R-wave) or ventricular pacing pulse is used as a surrogate of the measurement of maximum time separation of the E wave and A wave without A wave truncation in one embodiment of the hemodynamic profiling methods described herein.

The time interval between S1 and S2, i.e. S1-S2 time interval, represents a measurement of the systolic time interval (STI) corresponding to the ventricular isovolumic contraction (pre-ejection) and ejection phase of the cardiac cycle. This S1-S2 time interval may provide a surrogate measurement for stroke volume.

The third heart sound, S3, is associated with early, passive diastolic filling of the ventricles, and the fourth heart sound, S4, is associated with late, active filling of the ventricles due to atrial contraction. The third sound is generally difficult to hear in a normal patient using a stethoscope, and the fourth sound is generally not heard in a normal patient. Presence of the third and fourth heart sounds during an examination using a stethoscope may indicate a pathological condition. The S3 and S4 heart sounds may be used in generating patient hemodynamic profiles as they relate to diastolic function of the heart.

HS sensing module 12 is configured to receive analog signals from sensor 11 for sensing one or more of these heart sounds. For example, HS sensing module 12 may include one or more "channels" configured to particularly sense a specific heart sound based on frequency, duration, and timing of the heart sounds. For example, ECG/EGM sensing circuitry 14 may be used by control processor 16 to set HS sensing windows used by HS sensing module 12 for sensing the heart sounds. HS sensing module 12 may include sense amplifiers and filters for optimizing a signal-to-noise ratio of HS signals. Separate and unique amplification and filtering properties may be provided for sensing each of the S1 through S4 sounds to improve signal quality as needed.

In various embodiments, acoustical sensor 11 may be implemented as a microphone or a 1-, 2- or 3-axis accelerometer. In one embodiment, acoustical sensor 11 is implemented as a piezoelectric crystal mounted within an implantable medical device housing and responsive to the mechanical motion associated with heart sounds. Examples of acoustical sensors useful for heart sound monitoring that may be adapted for implementation with the techniques of the present disclosure are generally described in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), all of which patents are hereby incorporated by reference in their entirety. Practice of the methods and techniques described herein are not limited to a particular type of acoustical sensor. Acoustical sensor 11 may be any implantable or externally applied sensor responsive to one or more of the heart sounds generated as described in the foregoing and thereby produces an electrical analog signal correlated in time and amplitude to the heart sounds. The analog signal may be then be processed, which may include digital conversion, by HS sensing module 12 to obtain HS parameters, such as amplitudes or relative time intervals, as derived by HS sensing module 12 and/or control processor 16.

ECG/EGM sensing circuitry 14, coupled to at least one sensing electrode pair 13a included in electrodes 13, is provided to sense cardiac signals, e.g. P-wave or R-wave signals attendant to the depolarization of the atria and ventricles of the heart, respectfully. Sensing circuitry 14 is coupled to electrodes 13, which may include surface (skin) electrodes or subcutaneous electrodes for sensing ECG signals, or transvenous intracardiac electrodes for sensing cardiac EGM signals. ECG signals and EGM signals are referred to herein generally as "cardiac electrical signals". Cardiac electrical signals are sensed for use in timing pacing pulses delivered during HS recording for developing a hemodynamic response profile for the patient. Cardiac electrical signals may additionally be used for timing sensing windows used by HS sensing module 12 for obtaining HS signals. Cardiac electrical signals may additionally or alternatively be used by control processor 16 for determining time intervals relative to sensed heart sounds and these time intervals may be used in generating a patient hemodynamic response profile. Cardiac electrical signals are used in some embodiments for establishing heart rate conditions during which HS signals are acquired.

Pulse generator 15 is provided for delivering pacing pulses to the patient's heart via at least one electrode pair 13A of electrodes 13 using variable pacing parameters. HS recording is performed during variation of at least one pace control parameter to determine a hemodynamic response to changes in the pacing parameter. Accordingly, pulse generator 15 is coupled to cardiac pace electrodes, which may include temporary or chronically implanted electrodes, and may be skin electrodes, transvenous intracardiac electrodes, epicardial electrodes, or subcutaneous electrodes. The electrodes 13A used for delivering pacing pulses may be dedicated pacing electrodes, or may include shared electrodes with sensing electrodes 13B. Switching circuitry (not shown) may be used for selecting which electrodes 13 are coupled to ECG/EGM sensing circuitry 14 and pulse generator 15 and the polarity of such electrodes.

Pulse generator 15 is controlled by control processor 16 to deliver pacing pulses according to a test algorithm during which heart sounds are recorded for generating a hemodynamic response profile. Control processor 16 receives signals from ECG/EGM sensing circuitry 14 for use in controlling pulse generator 15 to deliver appropriately timed pacing pulses. Appropriately timed pacing pulses are pulses that are typically delivered at a rate greater than an intrinsic depolarization rate such that the pacing pulses control the timing of heart chamber activation. As such, a lower pacing rate and/or a pacing timing interval such as an AV interval or VV interval may be controlled such that a pacing pulse precedes an intrinsic activation of the heart. Appropriately timed pacing pulses are also delivered outside the vulnerable period to avoid risk of arrhythmia induction.

Control processor 16 may include any one or more of a microprocessor, a digital state machine, a digital signal processor (DSP), an application specific integrated circuit (ASIC), a field-programmable gate array (FPGA), or equivalent discrete or integrated logic circuitry. In some examples, processor 16 may include multiple components, such as any combination of one or more microprocessors, one or more controllers, one or more DSPs, one or more ASICs, or one or more FPGAs, as well as other discrete or integrated logic circuitry. The functions attributed to control processor 16 herein may be embodied as software, firmware, hardware or any combination thereof, implemented in a single device or distributed across two or more devices included in system 10, which may include one or more implantable devices, external devices, or a combination of both.

Control processor 16 includes a HS profiling module 18 for analyzing recorded heart sounds and classifying the patient according to the HS response to varying pace control parameters. HS profiling module 18 includes circuitry and/or computer-readable instructions for performing an algorithm for deriving HS parameters and trends or relative changes in HS parameters with changing pace control parameters. The response of a HS-derived parameter to a change in a pacing parameter is used to establish a hemodynamic profile of the patient. HS profiling module 18 derives one or more HS parameter trends with respect to pace control parameter(s) from one or more heart sounds and compares the derived HS parameter trend(s) to previously established profile classifications defined for classifying the patient's hemodynamic response profile. For example, in one embodiment, the amplitude of S1 may be measured during two or more different AV interval settings. Based on the response of the S1 amplitude parameter to changing AV interval, the patient may be classified as a potential responder to CRT therapy or as a predicted non-responder. For example, the HS parameter response profile may be a monotonically increasing response to increasing AV interval, monotonically decreasing, increasing then decreasing, or a relatively flat response.

Memory 22 stores algorithms and parameter values used by control processor 16 needed for carrying out the functions described herein. The response profile obtained for an individual patient may be categorized based on response profiles obtained from populations of patients known to be responders or non-responders to a particular cardiac therapy, such as CRT. Population-based HS profile classifications and corresponding matching criteria are stored in memory 22. Additional details and embodiments for generating a patient hemodynamic profile based on heart sounds and an associated classification thereof will be described below.

Control processor 16 is configured to establish control conditions under which HS signal data is acquired. The HS signal data acquired under multiple conditions allows a trend of one or more HS signal parameters as a function of the multiple conditions to be determined and used for generating a HS response profile. In some embodiments, the control conditions include multiple pace control parameter settings that the control processor 16 establishes for use by pulse generator 15 in delivering a pacing protocol during which HS signal data is acquired. Multiple pace control parameter settings may include, but are not limited to, pacing rate, AV interval, W interval, pacing electrode site, pacing vector and polarity.

Additionally or alternatively, control processor 16 is configured to establish multiple control conditions by verifying a physiological condition such as an intrinsic heart rate, patient posture, patient activity level or other sensed physiological condition. HS signal data is obtained under one or more control conditions, such as a multiple intrinsic heart rates, patient activity levels, patient postures or the like. Establishing a desired physiological control condition for acquiring HS data may be based on user input received by control processor 16 via communication circuitry or a user interface (e.g. included in reporting module 20) or automatically by control processor 16 in response to sensed physiological signals. As such, additional physiological sensors 28 may be required for providing control processor 16 with signals for verifying a desired control condition, such as a patient posture or patient activity level. A patient heart rate may be verified using ECG/EGM sensing module 14.

Reporting module 20 is configured to generate a report of a patient's hemodynamic response profile and classification based on heart sound evaluation. Reporting module 20 generally includes any device in communication with control processor 16 for receiving and displaying HS profile data. Reporting module may be included in an external programming device configured for bidirectional communication with control processor 16. The external programming device may include a graphical user interface or other display for displaying HS data received during bidirectional communication with control processor 16, which may be established via a wireless telemetry link. Reporting module 20 may alternatively include a computer configured to receive HS profile data for display on a computer screen. In some embodiments, reporting module may include a networked computer or communications device receiving HS profile data over a communications network and displaying HS profile data to a user. It is recognized that reporting module 20 may be implemented in a variety of configurations for conveying HS profile data to a clinician or other user. The particular equipment and software used for conveying HS profile data to a clinician will depend on the hardware and software architecture of system 10.

In some embodiments, system 10 includes a fully implantable device for collecting HS signals and generating the HS profile and an external device communicating with the fully implantable device for displaying and reporting HS profile information. In other embodiments, system 10 may be an external system, which may use surface electrodes and an external HS sensor or temporarily implanted electrodes and/or HS sensor. In still other embodiments, system 10 may be distributed between one or more fully implantable devices and one or more external devices.

Figure 2:
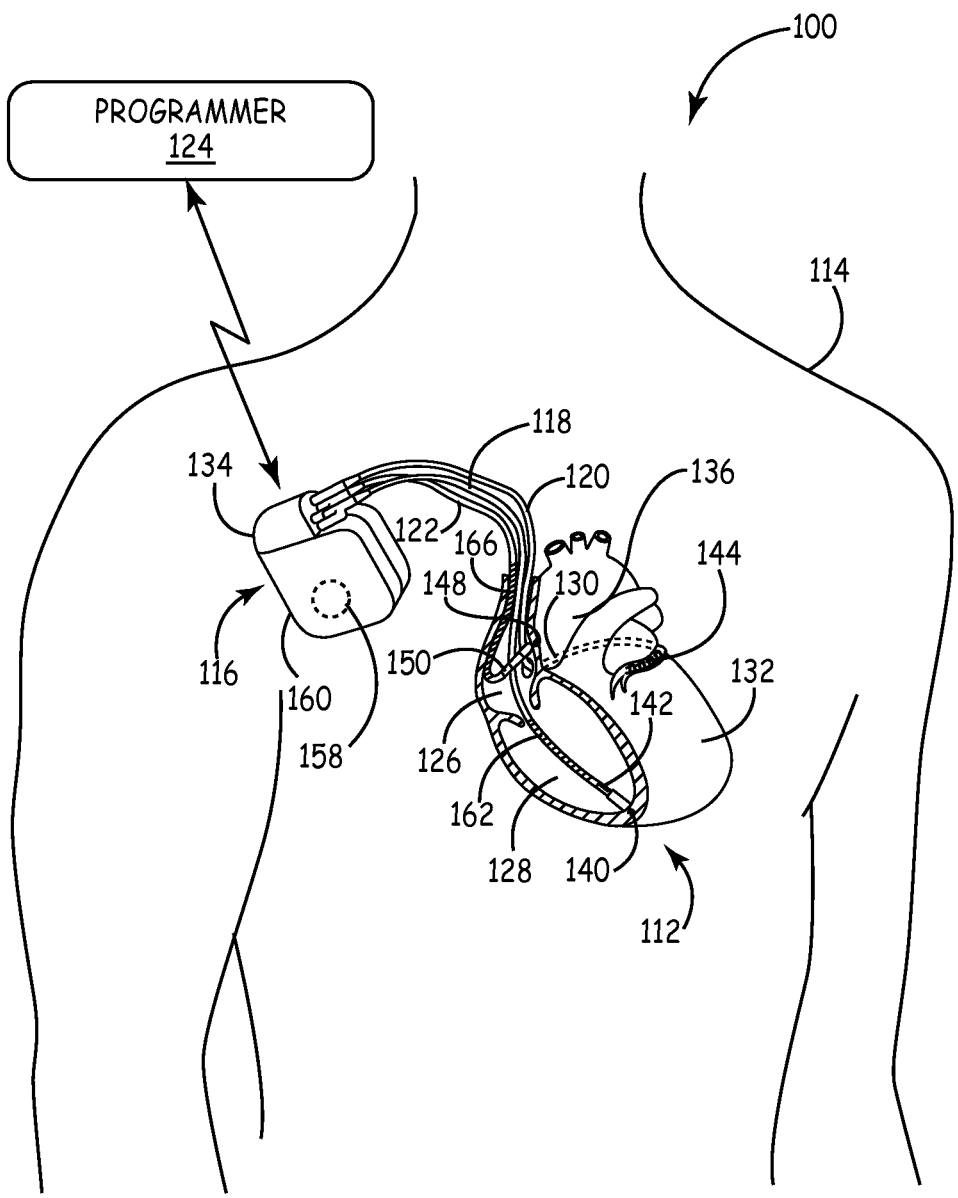
FIG. 2 is a schematic diagram of one embodiment of an implantable medical device (IMD) system in which techniques disclosed herein may be implemented to monitor and/or provide therapy to the heart of a patient.

FIG. 2 is a schematic diagram of one embodiment of an implantable medical device (IMD) system 100 in which techniques disclosed herein may be implemented to monitor and/or provide therapy to heart 112 of patient 114. System 100 includes IMD 116 and programmer 124. IMD 116 is coupled to leads 118, 120, and 122. IMD 116 may be, for example, an implantable pacemaker, cardioverter, and/or defibrillator that provides electrical signals to heart 112 via electrodes coupled to one or more of leads 118, 120, and 122. IMD 116 is capable of delivering at least single chamber ventricular pacing, and in the embodiment shown, is configured for multi-chamber pacing and sensing the in the right atrium (RA) 126, the right ventricle (RV) 128, and the left ventricle (LV) 132 using leads 118, 120 and 122.

IMD 116 delivers RV pacing pulses and senses RV intracardiac EGM signals using RV tip electrode 140 and ring electrode 142 positioned in the RV 128. RV lead 118 is shown to carry a coil electrode 162 which may be used for delivering high voltage cardioversion or defibrillation shock pulses. IMD 116 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes spaced along lead 120 for positioning along the left atrium (LA) 136 for sensing left atrial (LA) EGM signals and delivering LA pacing pulses.

IMD 116 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 116 may detect arrhythmias of heart 112, such as fibrillation of ventricles 128 and 132, and deliver defibrillation therapy to heart 112 in the form of electrical pulses. While IMD 116 is shown in a right pectoral implant position in FIG. 2, a more typical implant position, particular when embodied as an ICD, is a left pectoral implant position.

IMD 116 includes internal circuitry for performing the functions attributed to IMD 116 and a housing 160 encloses the internal circuitry. It is recognized that the housing 160 or portions thereof may be configured as an active electrode for use in cardioversion/defibrillation shock delivery or used as an indifferent electrode for unipolar pacing or sensing configurations. IMD 116 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

In the embodiment shown, IMD 116 is also configured for delivering CRT therapy, which may use a selected pacing vector for LV pacing that includes at least one electrode 144 on multipolar LV lead 120. Performing the methods described herein for classifying a patient's HS profile response to varying pacing parameters, however, does not require the use of an IMD capable of delivering CRT. For example, the methods described herein may be performed using a single or dual chamber pacemaker or ICD delivering pacing pulses at varying pace control parameters to measure at least one HS signal trend to the varying parameter for defining the patient's response profile. The HS response profile is compared to population-based profile definitions previously established to classify the response profile. The results of the HS profile classification may be used to identify patients that may benefit from CRT and may currently have a pacemaker or ICD. In illustrative embodiments, IMD 116 is configured to deliver pacing pulses in at least one ventricular chamber to allow HS signals to be obtained at varying pacing parameters, for example at varying AV intervals, VV intervals, or pacing vector. The profile of the HS response to varying pace parameters is used to predict a patient's response to a cardiac therapy such as CRT and indicate a therapy management approach for the given patient.

System 100 includes a HS sensor 158 which is shown to be incorporated in the IMD 116. As described above, HS sensor 158 may be a microphone, accelerometer, e.g. a piezoelectric transducer sensitive to the vibrations caused by motion of the blood and heart structures, or another acoustical sensor. In other embodiments, a HS sensor may be carried by an intra- or extravascular lead and is positioned in operative relation to heart 112 for obtaining signals representative of heart sounds.

IMD 116 may provide HS data to programmer 124 via wireless telemetry. HS data and/or a classification of the HS response profile may then be displayed to a user. Thus, the evaluation may be automated in the IMD system 100 and not require a specialized technician to perform the analysis, as required, for example, during echocardiography studies.

In some examples, programmer 124 may be a handheld device or a microprocessor based home monitor or bedside programming device. A user, such as a physician, technician, nurse or other clinician, may interact with programmer 124 to communicate with IMD 116. For example, the user may interact with programmer 124 to retrieve physiological or diagnostic information from IMD 116. A user may also interact with programmer 124 to program IMD 116, e.g., select values for operational parameters of the IMD. A user interacting with programmer 124 may request IMD 116 to perform a HS analysis algorithm and transmit results to programmer 124 or request retrieval of data stored by IMD 116 when HS analysis procedures are performed automatically by IMD 116 on a periodic basis. Programmer 124 receives data from IMD 116 for use in generating a display including information relating to HS data and/or a patient classification based on a HS signal response profile.

IMD 116 and programmer 124 communicate via wireless communication. Examples of communication techniques may include, for example, low frequency or radiofrequency (RF) telemetry, which may be an RF link established via Bluetooth, WiFi, MICS, or as described in U.S. Pat. No. 5,683,432 "Adaptive Performance-Optimizing Communication System for Communicating with an Implantable Medical Device" (Goedeke, et al). In some examples, programmer 124 may include a programming head that may be placed proximate to the patient's body near the IMD 116 implant site and in other examples programmer 124 and IMD 116 may be configured to communicate using a distance telemetry algorithm and circuitry that does not require the use of a programming head and does not require user intervention.

Figure 3:
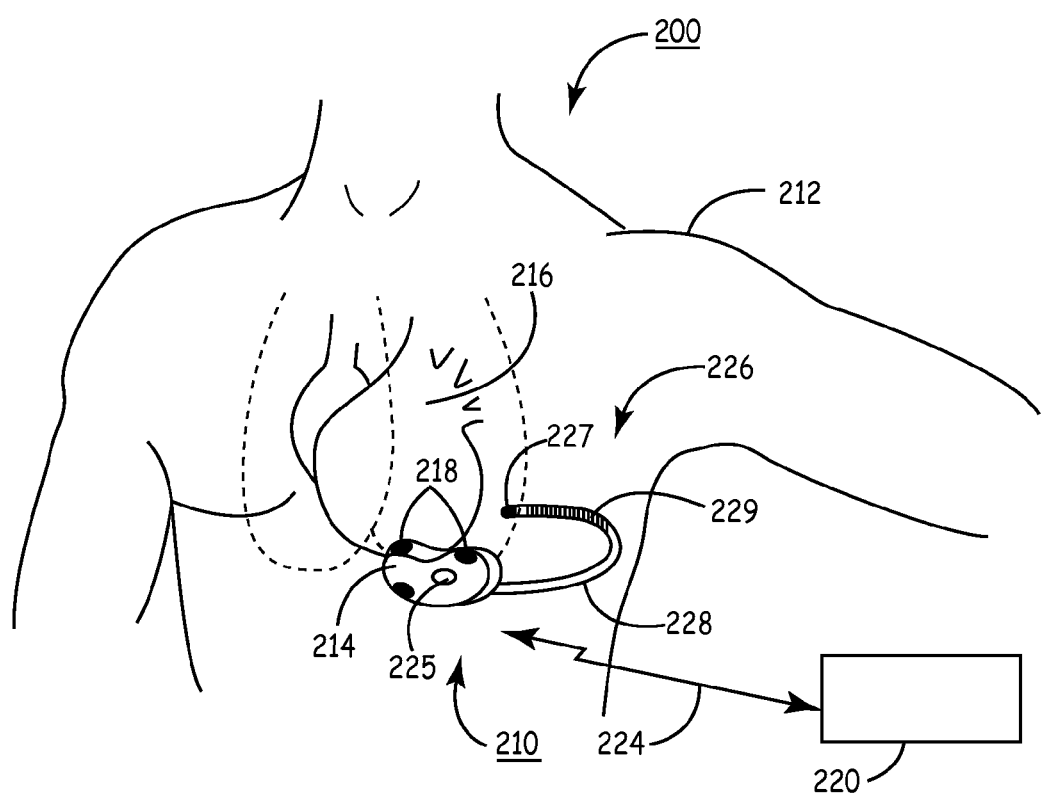
FIG. 3 is a schematic diagram of an alternative embodiment of a medical device system which may be used for performing the techniques disclosed herein.

FIG. 3 is a schematic diagram of an alternative embodiment of a medical device system which may be used for performing the techniques disclosed herein. In system 200, IMD 210 is embodied as a subcutaneous ICD (SubQ ICD) implanted in patient 212. SubQ ICD 210 includes a housing 214 generally shaped to promote ease of subcutaneous implant and minimize patient discomfort. SubQ ICD 210 is adapted to be implanted outside the ribcage of patient 212, anterior to the cardiac notch. An acoustical sensor 225 is shown mounted along the housing 214 of SubQ ICD 210. SubQ ICD 210 further includes a sensing electrode array 218 including three electrodes mounted on housing 214 for use in sensing subcutaneous ECG signals. It is recognized that in various embodiments, one or more electrodes, or no electrodes at all, may be incorporated on the SubQ ICD housing 214.

A subcutaneous sensing and cardioversion/defibrillation therapy delivery lead 228 is electrically coupled to SubQ ICD 210 via a connector block (not shown). Lead 228 includes a high voltage coil electrode 229 and may include one or more sensing electrodes 227 positioned near the distal end 226 of lead 228 such that the patient's heart 216 is positioned between the SubQ ICD 210 and electrodes 227 and 229.

The acoustical sensor 225 may be bonded to the external or internal surface of the housing 214 and electrically coupled to circuitry contained within the SubQ ICD housing via any necessary conductors and feedthroughs. Alternatively, sensor 225 may be attached to a hybrid circuit located inside the housing 214. In still other embodiments, acoustical sensor 225 may be carried by subcutaneous lead 228.

SubQ ICD 210 communicates with an external device 220, which may be embodied as a home monitor or programmer in telemetric communication with SubQ ICD 210 by communication link 224. Communication link 224 between the implanted device 210 and the external device 220 may be established as generally described above in conjunction with FIG. 2.

SubQ ICD 210 may be used to acquire HS signal data which may be processed by a processor included in SubQ ICD 210 or transmitted to external device 220 for processing according to the analysis methods described in greater detail below. If SubQ ICD 210 is able to pace the heart 216 using electrodes 218 and/or electrodes 227 and 229, HS signals may be acquired by SubQ ICD 210 during an algorithm that involves pacing heart 216 using different pacing control parameters to record the HS response and determine HS trends with changing pacing parameters. In some cases, SubQ ICD 210 may be capable of delivering high voltage shock pulses for cardioversion and defibrillation but not be capable of pacing heart 216 in which case a temporary pacing lead (not shown) may be inserted into heart 216 for pacing the heart according to a HS data acquisition algorithm.

Figure 4:
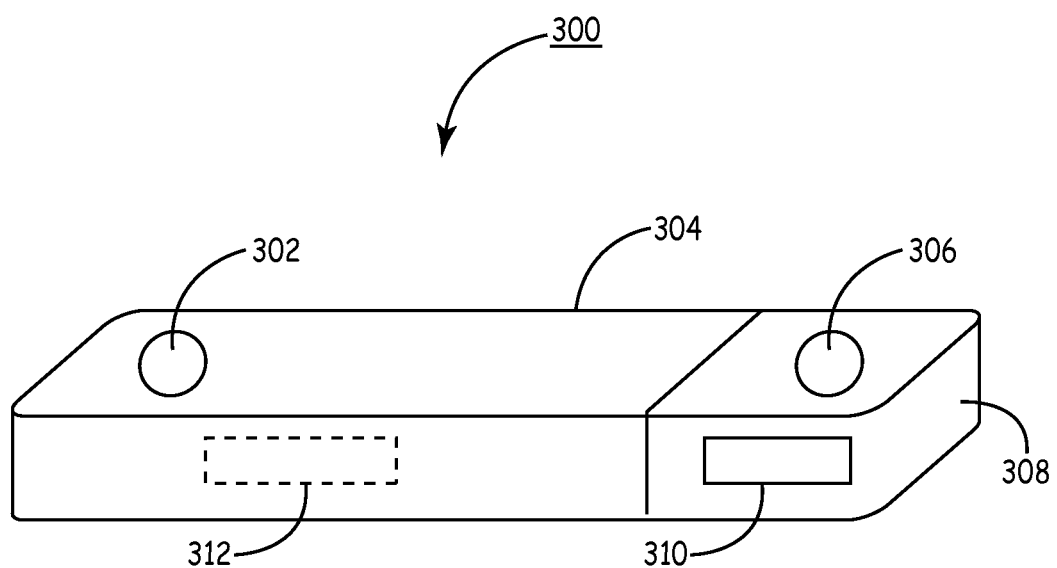
FIG. 4 is a schematic diagram of an IMD for monitoring a patient's heart which may be implemented in a system for determining a heart sound (HS) signal response to changing pacing parameters.

FIG. 4 is a schematic diagram of an IMD 300 for monitoring a patient's heart which may be implemented in a system for determining a HS signal response to changing pacing parameters. In this embodiment, IMD 300 is a subcutaneously implantable monitor that includes a housing 304 containing the electronic circuitry used for generating cardiac pacing pulses and for monitoring the patient's heart rhythm and which carries a molded plastic header 308. Alternatively, IMD 300 may be used in a system that includes another device and associated electrodes for delivering pacing pulses to the patient's heart according to a HS data acquisition algorithm, and IMD 300 is used only for sensing signals.

Housing 304 and header 308 each carry an electrode 302 and 306, respectively for monitoring cardiac electrical signals (and optionally delivering pacing pulses). Also mounted in the header 308 is an antenna 310 for use in communicating between IMD 300 and an external programmer or other device configured to receive HS signal data from IMD 300. IMD 300 includes an acoustical sensor 312 positioned along or within housing 304 which is used for collecting HS signals during cardiac pacing using varying pacing control parameters. In other embodiments, a lead may extend from IMD 300 carrying a HS sensor and/or ECG sensing and/or pacing electrodes.

Cardiac ECG signals are acquired using electrodes 302 and 306 and HS signals are acquired using sensor 312. IMD 300 collects the HS signals and may transmit raw or processed signals using antenna 310 and associated communication circuitry to another device, implanted or external for classification according to population-based HS response profile definitions.

Figure 5:
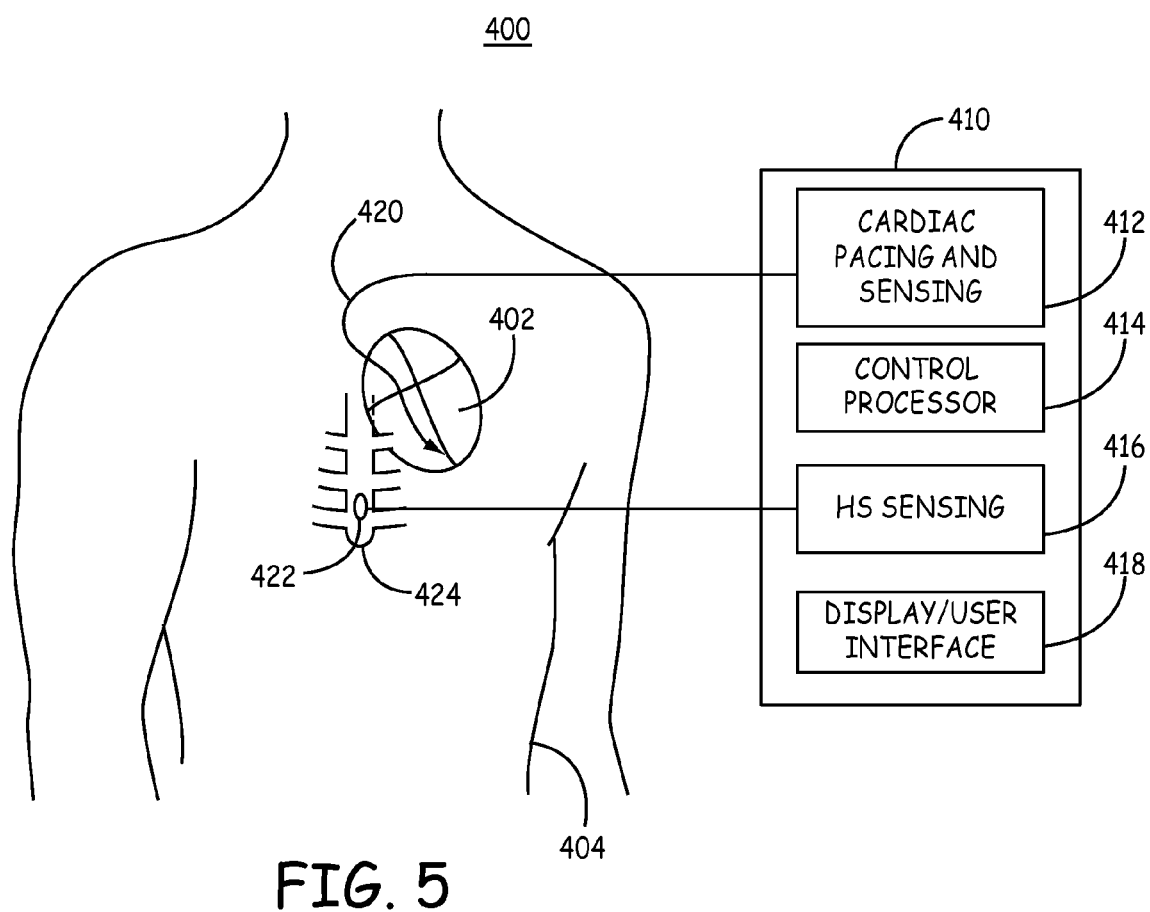
FIG. 5 is a schematic diagram of another embodiment of a medical device system which may be configured to perform the disclosed techniques described herein.

FIG. 5 is a schematic diagram of another embodiment of a medical device system 400 which may be configured to perform the disclosed techniques. System 400 is primarily an external system including an external programmer or computer 410 having a cardiac pacing and sensing module 412, control processor 414, HS sensing module 416 and display and user interface 418. The modules 412, 414, 416 and 418 may be included in a single external programming or computing device or distributed across multiple external devices.

A temporary cardiac pacing lead 420 may be advanced into the RV of the patient's heart 402. The pacing lead 420 is coupled to a cardiac pacing and sensing module 412 for sensing cardiac EGM signals and deliver pacing pulses according to a HS signal acquisition algorithm. Lead 420 is provided with at least one electrode for sensing and pacing the heart 402 in bipolar combinations (when 2 or more electrodes are carried by lead 420) or in a unipolar combination with an external surface electrode, such as a patch electrode (not shown). Alternatively, surface electrodes may be positioned on patient 404 for sensing cardiac signals and pacing the heart.

An acoustical sensor 422 is provided as a wireless or hard-wired sensor coupled to HS sensing module 416. Acoustical sensor 422 may be positioned against the patient's skin at any location that enables HS signals to be acquired with an acceptable signal to noise ratio. In one example, sensor 422 is generally positioned over the patient's sternum 424. Sensor 422 is shown as an external sensor but an acoustical sensor may alternatively be carried by lead 420.

Control processor 414 controls cardiac pacing and sensing module 412 and HS sensing module 416 to acquire HS signals during a pacing algorithm that includes at least two different settings of a pacing control parameter. The control processor 414 and/or processing circuitry included in HS sensing module 416 determines a HS signal response profile, compares the profile to stored profile definitions for classifying the patient's response profile for use in predicting a patient's response to a cardiac therapy, and provides an indication of how the therapy should be managed or optimized. The results of the HS signal analysis and classification may be displayed to a user by display 418. A user interacting with device 410 may initiate a HS signal analysis that is then performed automatically by system 400. The user may select pacing parameters to be automatically adjusted during the HS signal acquisition algorithm or the control processor 414 may automatically set the pace parameter(s) that are varied and select different settings for the parameter(s). Device 410 may be a networked device that allows display and user interface 418 to be located remotely from patient 404 so that a clinician or other user is able to evaluate the patient's HS response data and classification remotely.

Figure 6:
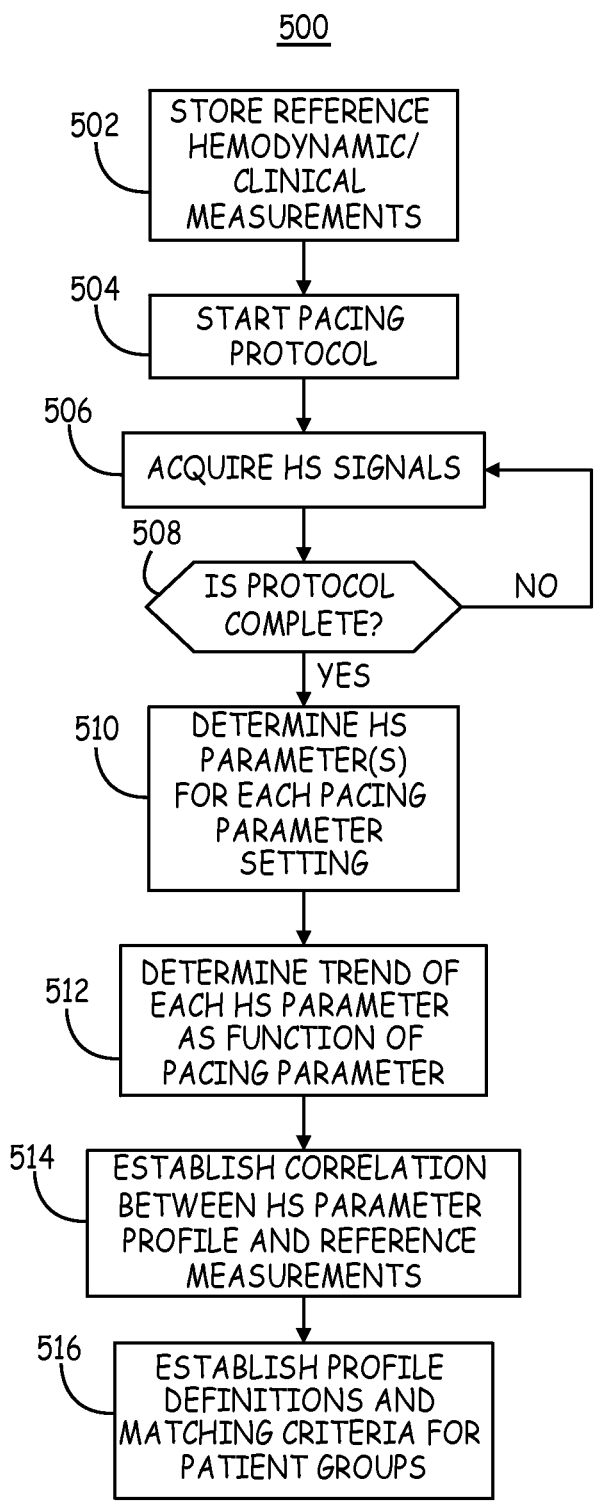
FIG. 6 is a flow chart of a method for establishing HS classification profile definitions according to one embodiment.

FIG. 6 is a flow chart 500 of a method for establishing population-based HS classification profile definitions according to one embodiment. Flow chart 500 and other flow charts presented herein are intended to illustrate the functional operation of a medical device system, and should not be construed as reflective of a specific form of software or hardware necessary to practice the methods described. It is believed that the particular form of software, firmware and hardware will be determined primarily by the particular system architecture employed and by the particular sensing and pacing delivery methodologies employed by the system. Providing software to accomplish the described functionality in the context of any modern medical device system, given the disclosure herein, is within the abilities of one of skill in the art.

Methods described in conjunction with flow charts presented herein may be implemented in a computer-readable medium that includes instructions for causing a programmable processor included in the medical device system to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The method shown by flow chart 500 is performed in a population of patients that have received a cardiac therapy, such as CRT, to establish HS profile definitions and matching criteria used to identify potential therapy candidates. Reference measurements that can be used as standardized measurements for categorizing patients receiving the therapy are stored at block 502. Reference measurements may include hemodynamic measurements, such as left ventricular end systolic volume (LVESV), left ventricular ejection fraction (LVEF), cardiac output, stroke volume, pressure-volume loops, or other hemodynamic or cardiac function-related measurements obtained using echocardiography or catheterization methods, for assessing the patient before and after starting the therapy. Reference measurements may additionally or alternatively include clinical measurements such as results of maximal or submaximal exercise testing, quality of life assessments, NYHA classification or other assessments used to track the patient's heart failure progress. Reference measurements may include objective hemodynamic measures and relatively more subjective clinical measures.

At block 504, a HS data acquisition algorithm is initiated in an individual patient of the population of patients by starting a pacing protocol that includes varying at least one pacing control parameter. The pacing protocol may include varying one or more timing-related pace parameters, such as AV interval and W interval, and/or one or more other pacing control parameters such as pacing site or pacing vector. During pacing at each pace parameter setting or combination of settings, HS signals are acquired at block 506. HS signals may be acquired for one or more cardiac cycles during pacing at a particular parameter setting and may be ensemble averaged over a predetermined number of cycles in one example.

At block 510, a processor is enabled to compute at least one HS parameter for each pacing parameter setting. As described previously HS parameters may correspond to one or more of the heart sounds S1 through S4 and may relate to an amplitude, frequency content, relative time interval or any combination or ratio thereof. In one example, the S1 peak amplitude, the S1-S2 time interval between selected fiducial points on each of the S1 and S2 signals, and a V-S2 time interval between a ventricular sensed or paced event and a fiducial point of the S2 signal waveform are measured.

The trend of each HS parameter vs. the varying pace control parameter is determined at block 512. A trend may be monotonically increasing, monotonically decreasing, generally bell-shaped (i.e. having an increasing and decreasing portion) which may be upright or inverted, generally flat or unchanging, or including both a generally flat and a changing (increasing, decreasing or both) portion. The combination of one or more trends for each HS parameter as a function of the selected pacing parameter(s) is considered a HS profile for the given patient.

At block 514, clusters or groupings of the population of patients based on individual HS profiles are identified using statistical analysis methods. The clusters or groupings are compared to the reference measurements to allow the clusters or groupings to be classified based on the patient's response to therapy. In one example, groupings of HS profiles may be classified as "responders" and "non-responders". Classifications of responders and non-responders would be based on the reference measurements. Based on clinical data or clinician preference, a hemodynamic or clinical measurement or any combination thereof may be used to define patients that are clearly responders to the therapy and patients that are non-responders or cannot be clearly identified as responders. For example, responders may be defined as patients that demonstrate at least a 10%, 15% or other threshold decrease in LVESV and an improvement in NYHA functional class. Responders may alternatively be defined as patients that show at least a threshold improvement in a six-minute walk test. A non-responder may be a patient that does not present a threshold improvement in LVESV and remains at the same or worse NYHA functional class.

In another embodiment, a "full responder" is defined as a patient having a clinical composite score of "improved" and a LVESV decrease of at least 10% of a baseline LVESV measurement. A "partial responder" is a patient having an "improved" clinical composite score but a decrease in LVESV that is less than 10% of the baseline LVESV. A "non-responder" is a patient having a "worsened" or "unchanged" clinical composite score and a LVESV that is worsened, unchanged or a decrease less than 10% of the baseline LVESV for that patient. The clinical composite score classifications are defined as: 1) "Worsened" if the patient dies, is hospitalized due to or associated with worsening heart failure, demonstrates worsening NYHA class compared to baseline, demonstrates moderate to marked worsening of patient global assessment score, or permanently discontinues CRT due to or associated with worsening HF; 2) "Improved" if the patient has not worsened and demonstrates improvement in NYHA class or moderate to marked improvement in patient global assessment score (e.g., patient subjective self-assessment or questionnaire); and 3) "Unchanged" if the patient is neither improved or worsened based on NYHA class or patient global assessment score.

The definition of a responder and a non-responder according to hemodynamic and/or clinical measurements may change over time as clinical data is amassed and may vary between clinical centers or physicians. A correlation between the HS profile and the reference measurements separating therapy responders and non-responders is determined at block 514.

Additional or alternative patient groupings may be defined. For example, one or more subsets of the responder and non-responder groups may be defined. Of the responders, acute responders, for example those patients showing immediate improvement within 1 day of initiating the therapy, may be separated from chronic responders, those patients showing long-term improvement for example after 6 months of therapy. Chronic responders may or may not include acute responders. Other responder subsets that may be defined may include "super-responders" and "normal responders"; "progressive improvers" and "non-progressive improvers". Super-responders may be defined as those responders that meet a higher level of tiered thresholds of hemodynamic and/or clinical reference measurements that represent even greater improvement as opposed to normal responders that meet a minimum set of criteria for being classified as responders. Progressive improvers would be those that show continuing improvement over time and non-progressive improvers are those patients that present an initial improvement adequate to be classified as a responder but no further progression in improvement.

Of the progressive improvers, "acute responders" and "acute non-responders" may be identified. A progressive improver may be an acute responder that continues to improve or a patient that does not improve acutely but does show chronic improvement that continues to progressively improve over time. It is recognized that numerous classifications and subsets of those classifications may be defined according to reference measurements and these classifications will at least in part depend on the therapy being evaluated and the state of clinical knowledge in defining and clearly classifying therapy responses.

Based on the reference measurement-based classifications and the clustered HS profiles, profile definitions and classification matching criteria are defined at block 516. Matching criteria may be defined in numerous ways such as logic combinations of HS parameter threshold requirements, hierarchical threshold requirements, weighted combinations of the HS parameter values meeting a threshold requirement, or each HS parameter individually meeting a threshold requirement or range. Once HS profile definitions and matching criteria for a given patient classification are established at block 516 based on a population of patients, individual patients may be evaluated to predict a patient's response to the therapy and therapy management recommendations can be made. For example, in addition to recommending CRT therapy, recommended management of CRT for a particular patient may include whether the paced AV interval should be set longer than or close to the intrinsic AV interval or if an optimized AV interval different than the intrinsic AV interval should be identified and routinely optimized.

Figure 7:
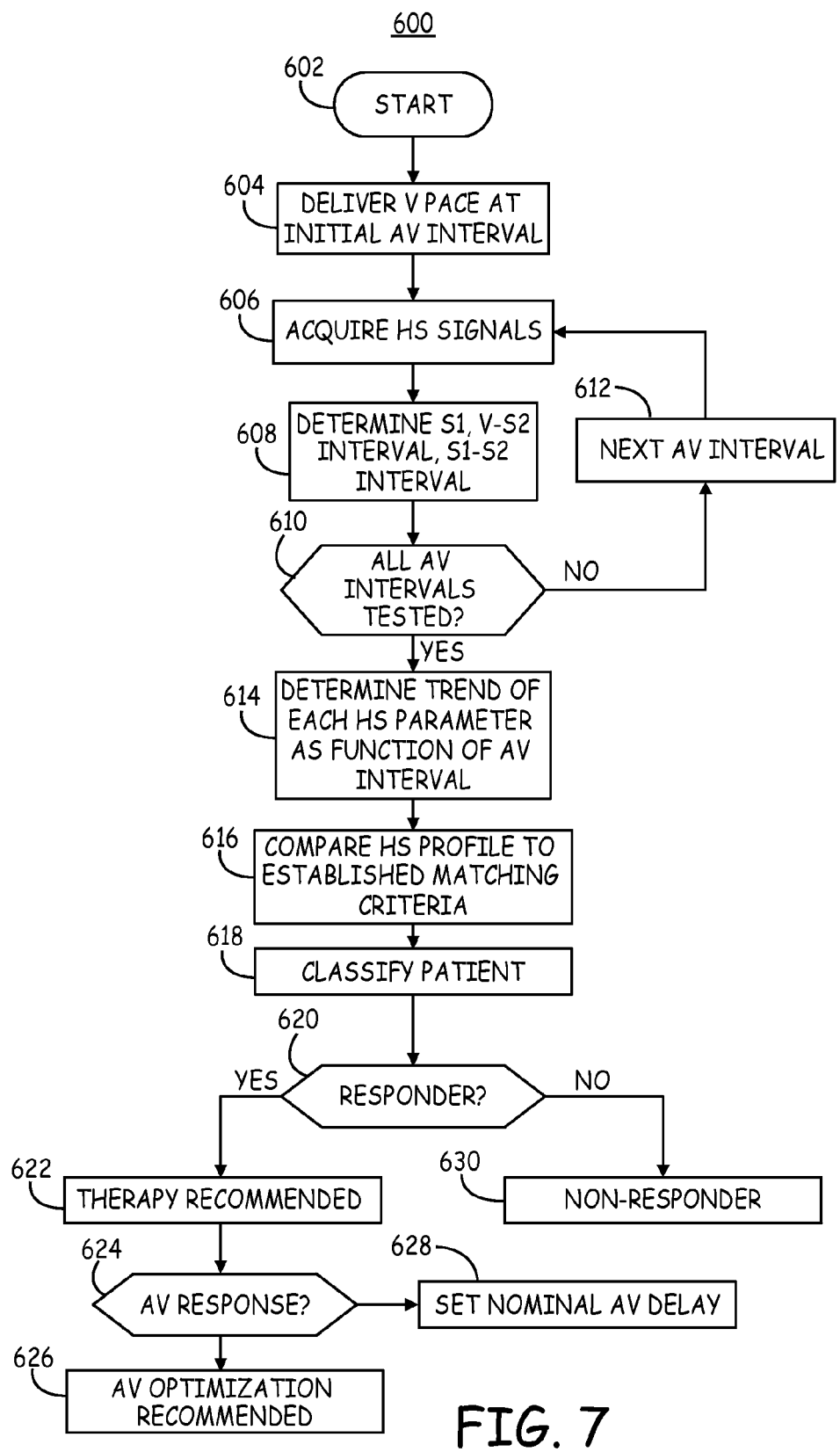
FIG. 7 is a flow chart of a method for acquiring HS signal data for classifying a patient's HS profile according to one embodiment.

FIG. 7 is a flow chart 600 of a method for acquiring HS signal data for classifying a patient's HS profile according to one embodiment. The process is initiated at block 602. The process may be initiated automatically on a periodic basis in a patient implanted with a pacing device, such as a pacemaker or ICD. HS data may be acquired by the implanted device and a classification made by the device with associated recommendations or the HS data may be transmitted to an external device for determining the patient's HS profile and associated classification. Alternatively, the process is initiated at block 602 in response to a command received by an external device, which may be a user-entered command requesting a HS profile analysis. The external device may provide pacing and data analysis or operate cooperatively with an implanted device for delivering pacing and performing the HS analysis.

At block 604, a pacing sequence is initiated. In one embodiment, ventricular pacing is delivered at an initial AV interval. It is understood that an initial AV interval may be selected at block 604 by first measuring an intrinsic AV interval in a patient having intact AV conduction, i.e. no AV block. An initial AV interval may be a default pacing interval, the last programmed AV interval, or a minimum or maximum AV interval to be tested. During pacing at the initial AV interval, HS signals are acquired at block 606 using an implanted or external acoustical sensor. Ventricular pacing may be delivered in the RV, LV or both with the AV interval controlling an interval between an atrial sensed event (P-wave) or an atrial pacing pulse and the ventricular pacing pulse.

HS signals may be acquired for multiple cardiac cycles to enable ensemble averaging or averaging of HS parameter measurements taken from individual cardiac cycles. It is understood that amplification, filtering, rectification, noise cancellation techniques or other signal processing steps may be used for improving the signal-to-noise ratio of the HS signals and these steps may be different for each of the heart sounds being acquired, which may include any or all of S1 through S4.

In one embodiment, S1 and S2 are recorded and HS parameters are measured at block 608. The amplitude of S1, the V-S2 interval, and the S1-S2 interval are measured. The presence of S3 and/or S4 may additionally be noted or measurements of these signals may be made for determining related parameters.

HS signal parameters are determined for at least two different AV intervals. The next AV interval is selected at block 612. Ventricular pacing at the new AV interval is applied, and HS signals are acquired at block 606. When all AV intervals to be tested have been applied, as determined at decision block 610, the trend of each HS parameter with changing AV interval is determined at block 614.

In alternative embodiments, HS signals may be acquired when other pacing parameters are adjusted rather than (or in addition to) AV interval. If biventricular pacing is available, a VV interval may be varied. If multiple pacing vectors are available, pacing site in a heart chamber and/or pacing vector may be varied. Of course the HS signals acquired during individual patient analysis will be acquired using the same or similar pacing protocol used for establishing the population-based profile definitions and matching criteria.

At block 616, the HS profile determined for the individual patient is compared to the established HS profile matching criteria. Based on this comparison, the patient is classified according to one of the patient groups at block 618, e.g. responder or non-responder and optionally a subset thereof as described above. Criteria for determining a match between a HS profile and a patient group may be defined for determining a closest match. For example, in order to classify a patient in a particular group, at least one HS trend of the HS profile must match the group profile. The group profile having the highest number of HS trends matching the HS trends of the individual patient may be identified as the closest match. In some embodiments, logic-based algorithms or weighted or hierarchical criteria may be applied to determine a closest matching patient group classification to the individual patient's HS profile.

If the patient is classified as a responder, as determined at decision step 618, CRT is recommended at block 622. At decision block 624, the HS profile is evaluated to determine if a hemodynamic response to AV interval optimization is expected. If the HS profile presents a trend in a HS parameter previously established as being indicative or predictive of a hemodynamic improvement in response to AV interval, then AV optimization for the patient is recommended at block 626. In some patients, a HS parameter trend may be a flat trend or a trend that is associated with a deleterious hemodynamic effect for AV intervals shorter than the intrinsic AV conduction time. In such patients, an intrinsic AV interval may be most beneficial making AV optimization methods unnecessary and perhaps even causing decreased hemodynamic benefit of CRT. In patients that AV optimization to an interval shorter than the intrinsic AV interval is not recommended, the AV interval is set to a nominal value at block 628, which may be a maximal programmable value to allow the intrinsic AV conduction to dominate.

The method shown by flow chart 600 may be performed in a patient having a single chamber pacing device or ICD that is not configured to delivery CRT. The patient may be periodically monitored using the method shown by flow chart 600 to determine if the HS profile substantially matches a profile previously established as a CRT responder profile. If the HS profile indicates a CRT responder, the patient may be upgraded to an IMD including CRT delivery capabilities. Thus, in response to a therapy recommendation at block 622, a clinician may prescribe CRT. When the HS profile analysis is performed in a patient not having a CRT device, HS signal analysis allows patients that may benefit from CRT to be identified, independent of other patient selection criteria such as NYHA class, QRS width, etc.

Figure 8:
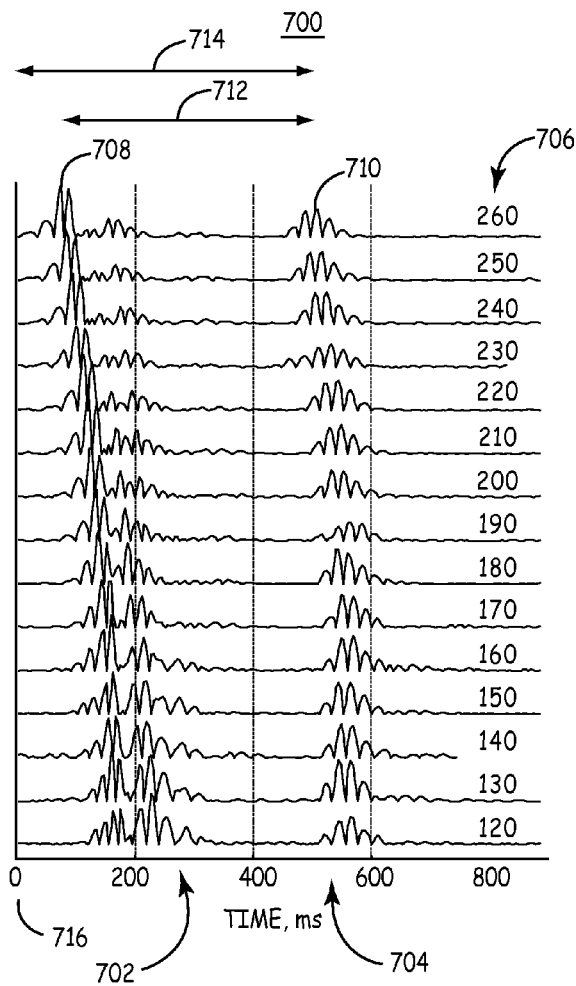
FIG. 8 is a display of HS signals recorded for varying AV interval settings.

FIG. 8 is a display 700 of HS signals recorded for varying AV interval settings. The display 700 may be generated for viewing by a clinician on a programmer or other external device in some embodiments. S1 signals 702 and S2 signals 704 are recorded for AV interval settings 706 ranging from 120 ms to 260 ms in this example. As can be observed on display 700, the amplitude and morphology of both S1 702 and S2 704 change with varying AV interval. Additionally, the S1-S2 time interval 712 changes with AV interval. The S1-S2 time interval 712 is shown as being measured between a detected maximum peak amplitude 708 and maximum peak amplitude 710 of each of the respective S1 702 and S2 signals 704. In various embodiments, different fiducial points may be defined for detection of S1 and S2 signals for determination of an S1-S2 time interval 712.

Time "0" 716 corresponds to the time of the ventricular pacing pulse. A V-S2 time interval 714 is also observed to change with different AV interval settings 706. The V-S2 time interval 714 may be measured as a time interval between an RV pacing pulse or sensed RV R-wave and the S2 peak amplitude 710, or an LV pacing pulse or sensed LV R-wave and S2 peak amplitude 710 or another fiducial S2 signal point.

The HS parameters S1 amplitude 708, S2 amplitude 710, S1-S2 interval 712 and V-S2 interval 714 are determined for each AV interval setting 706. The trend of one or more of the HS parameters with AV interval is determined as the HS profile for the given patient.

Figure 9:
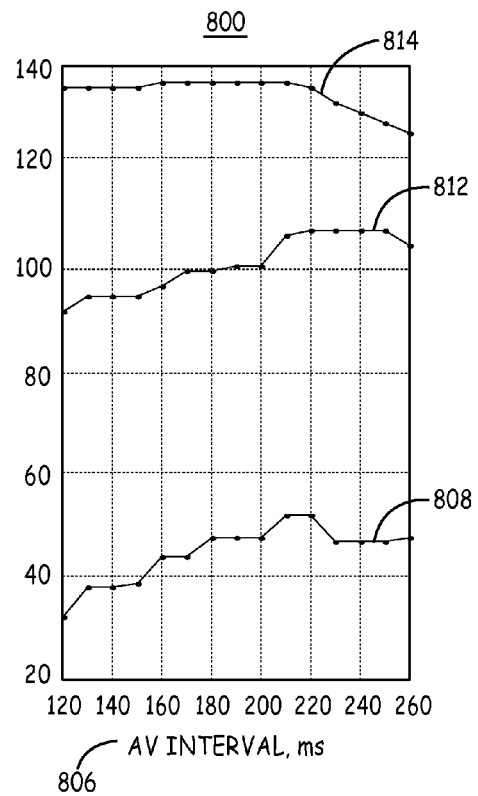
FIG. 9 is a HS profile plot generated from the data shown in FIG. 8.

FIG. 9 is a HS profile plot 800 generated from the data shown in FIG. 8. The S1 amplitude trend 808, S1-S2 interval trend 812, and V-S2 interval trend 814 are each shown plotted as a function of AV interval 806. The combination of the three HS parameter trends 808, 812 and 814 defines the patient's HS profile. As can be observed, the S1 amplitude trend 808 is generally bell shaped having a peak at approximately 220 ms. S1-S2 interval trend 812 is generally increasing, reaching a peak at approximately 220 ms. The V-S2 interval trend 814 is flat with a sudden change to a decreasing trend at approximately 220 ms. This profile of a bell-shaped S1 amplitude trend, an increasing S1-S2 interval, and a V-S2 trend exhibiting a flat portion and sudden change to a decreasing portion is matched to a profile definition separating patient groups to predict whether, based on this HS profile response to AV interval, the patient is expected to be a responder or non-responder to CRT.

In one embodiment, a V-S2 interval trend that exhibits a sudden change, e.g. from a substantially flat trend to a suddenly decreasing trend, represents a patient that will benefit from AV interval optimization during CRT. A classification for such a patient may be a progressively improving responder. When the V-S2 interval trend exhibits a sudden change, a recommendation for CRT therapy with regular AV optimization is recommended in one illustrative embodiment.

Figure 10:
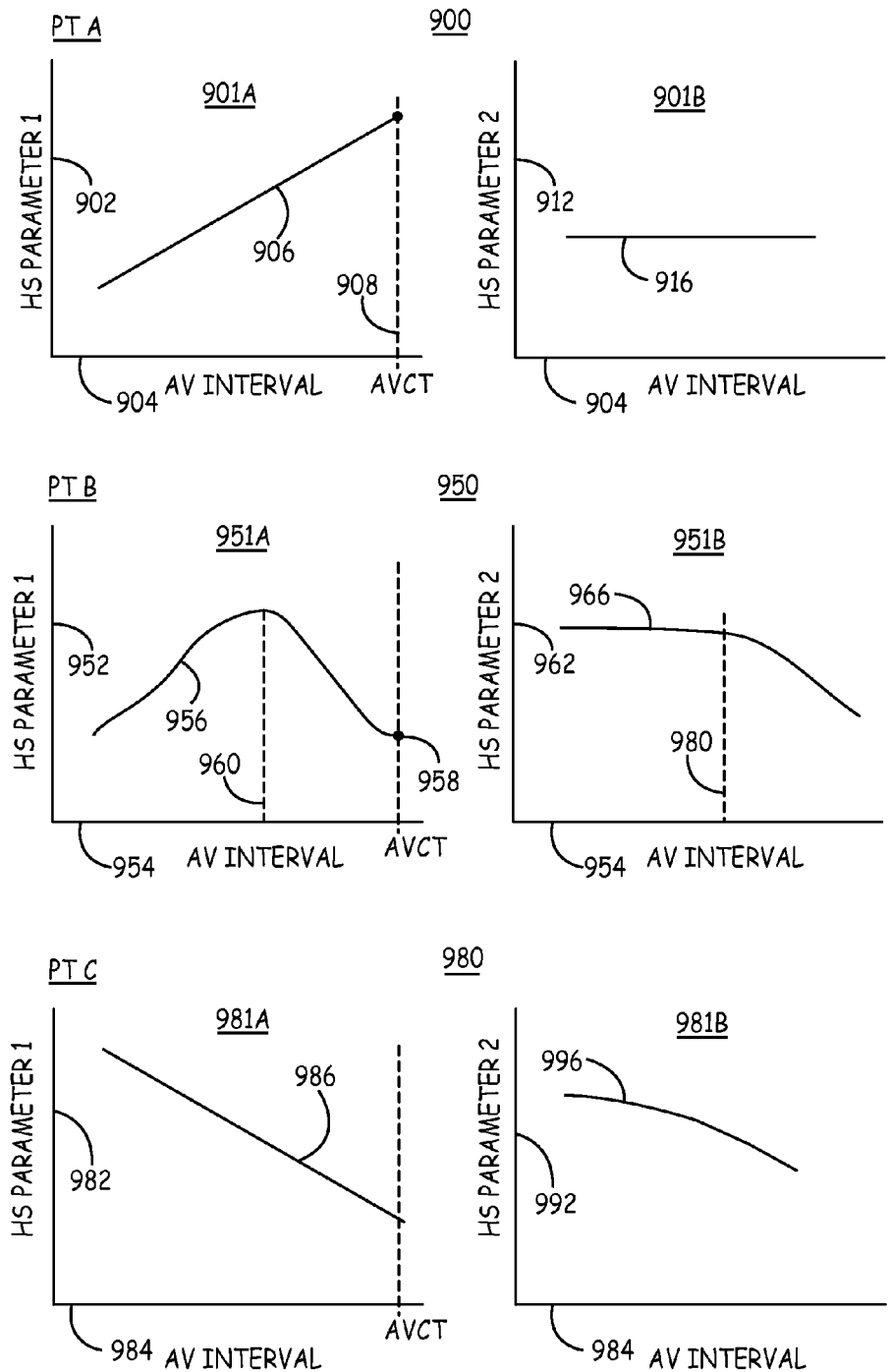
FIG. 10 graphically depicts HS profiles for two hypothetical patients.

FIG. 10 depicts HS profiles 900, 950 and 980 for three hypothetical patients, Pt A, Pt B, and Pt C, respectively. The HS profiles 900, 950 and 980 are each shown to include two HS parameter trends 901A and 901B, 951A and 951B, and 981A and 981B, respectively. HS parameter 1 and HS parameter 2 are two different HS parameters derived from HS signals and are shown plotted as functions of AV interval 904, 954, 984. HS parameter 1 may correspond, for example, to S1 amplitude or another HS parameter that positively correlates with a hemodynamic-related measurement. S1 correlates, for example, to ventricular contractility. HS parameter 2 may correspond, for example, to the V-S2 time interval or another HS-derived time interval that is correlated to ventricular systolic function, such as stroke volume or ejection time. The V-S2 interval trend may indicate an optimal AV interval at the inflection point of the trend when a sudden change in the slope or trend is observed. This AV interval corresponding to the V-S2 interval inflection point is strongly correlated to an optimal AV interval identified by Doppler echocardiography based on maximizing the separation between the E wave and A wave without A wave truncation.

The HS profile 900 for Pt. A presents a monotonically increasing trend 906 for HS parameter 1 902 as a function of AV interval 904 and a substantially flat response 916 of HS parameter 2 912 to varying AV interval 904. The HS profile 950 for Pt. B presents a bell-shaped trend 956 for HS parameter 1 952 as a function of AV interval 954 and a substantially flat, suddenly changing to a decreasing trend 966 for HS parameter 2 962. In other embodiments, HS profiles 900 and 950 may include additional HS parameter trends. In the given example, both profiles 900 and 950 may match a HS profile classification of "responder" based on the population-based profile definitions and matching criteria. Both patients A and B may be recommended for CRT, but belong to different subsets of the responder group due to their differing profiles. The different profiles 900 and 950 may indicate different subsets of the responder classification that indicate how the patients will respond, for example acutely or chronically, progressive improvement or non-progressive improvement.

In one embodiment, the different profiles 900 and 950 represent different indications for how CRT should be managed. In the case of patient A, HS parameter 1 902 is shown to monotonically increase with a peak occurring at the intrinsic AV conduction time (AVCT) 908. Setting an AV interval shorter than the intrinsic AVCT 908 may result in a negative hemodynamic effect according to the trend 906. Accordingly, CRT without AV interval adjustment is recommended for patient A. AV interval settings that are less than the intrinsic AVCT are not recommended; setting a maximum AV interval to allow intrinsic AV conduction is recommended due to the HS parameter 1 trend 906.

In patient B, an improvement in HS parameter 1 952 is seen when the AV interval is shorter than the intrinsic AVCT 958; a maximum improvement in HS parameter 1 952 occurs at an AV interval indicated at 960. Additionally, the sudden change in the trend of HS parameter 2 962 may indicate that this patient will benefit from optimizing AV interval. In one example, HS parameter 2 is the V-S2 time interval and is used as a surrogate for the E-A interval in Doppler echocardiography-based CRT optimization for maximizing LV filling. As such, CRT including AV interval optimization is recommended in patient B. Thus, based on the two different profiles 900 and 950, both may be classified as responders but with different sub-classifications indicating a recommended therapy management approach.

The profile 980, including a decreasing trend 986 for HS parameter 1 and a decreasing trend 996 for HS parameter 2, represents a profile that does not closely match a "responder" profile. Pt C is classified as a "non-responder" in this illustrative example. The patient would not be recommended for CRT. Having this HS profile data may allow a clinician to select (or not select) patients for CRT even when other clinical or hemodynamic measures, such as NYHA class or LVEF, may not indicate (or indicate) a possible CRT candidate.

The particular profiles shown in FIG. 10 and other profiles described or presented herein are illustrative in nature. The type of HS profiles, profile matching criteria, and the classifications used in a particular embodiment will depend on the therapy and the patient population used to generate the reference measurements and profile definitions.

Figure 11:
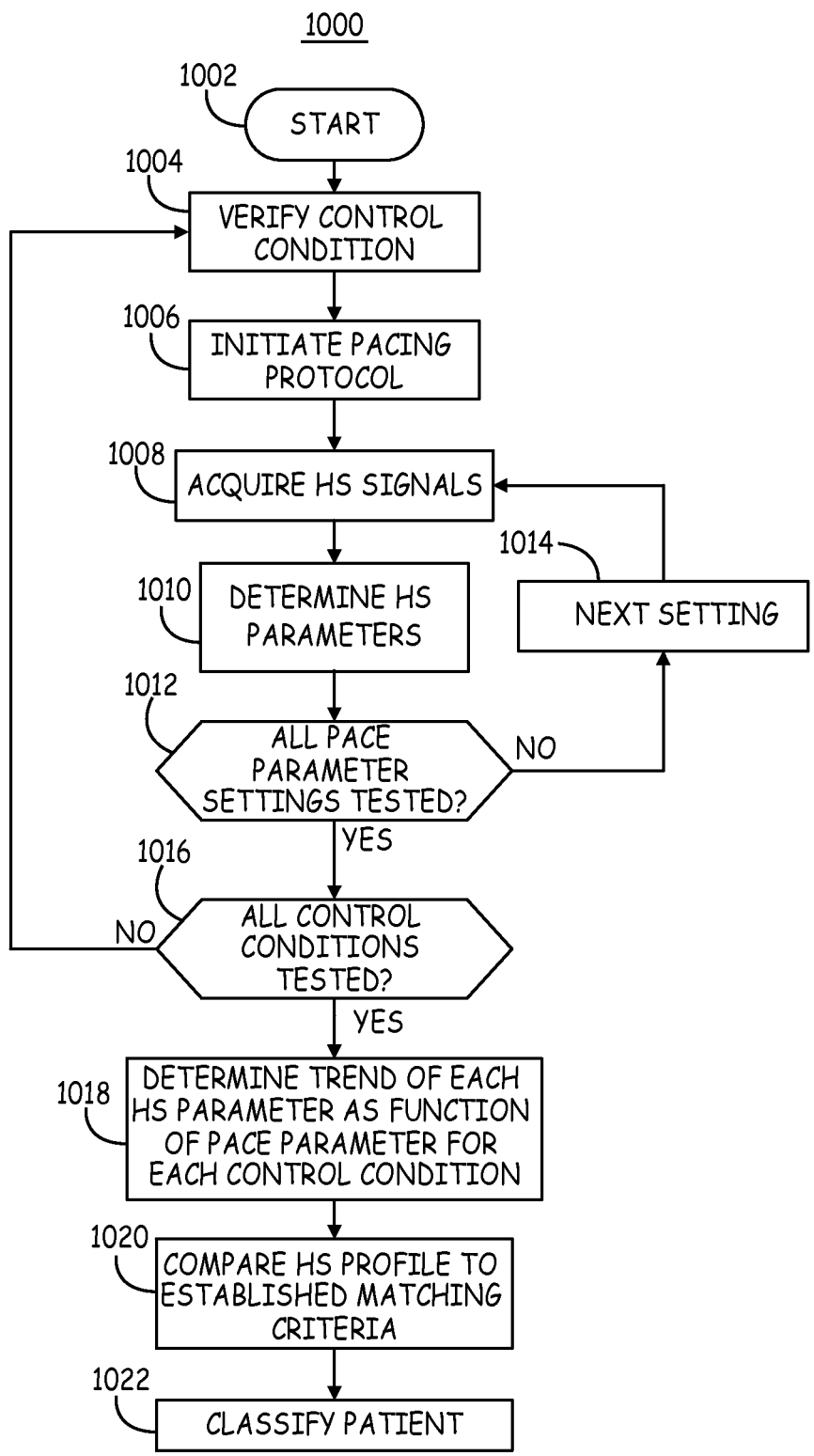
FIG. 11 is a flow chart of a method for generating a HS profile for a patient according to an alternative embodiment

FIG. 11 is a flow chart 1000 of a method for generating a HS profile for a patient according to an alternative embodiment. At block 1002 the process is initiated in response to user input or automatically, e.g. at a periodic time interval. At block 1004, a physiological control condition is verified. HS signal data may be acquired during one or more different control conditions. HS signal data may be acquired during a desired control condition, e.g. a resting heart rate and supine position, to produce comparable HS response profiles over time in a given patient and between a patient and the population-based profile classifications.

In other embodiments, HS signal data is acquired for multiple physiological control conditions to allow a HS response profile to be generated that includes HS parameter trends measured for different control conditions. For example, a HS parameter trend with respect to a pace control parameter when the patient is in a supine condition and a trend of the same HS parameter trend with respect to the pace control parameter measured when the patient is in an upright condition may be different. Differences in a given HS parameter trend with respect to a pace control parameter due to changing patient posture may provide meaningful HS response profile information for classifying a patient according to a predicted response to a heart failure therapy.

In one embodiment, a HS response profile is generated over different heart rates. The heart rates may be paced heart rates or intrinsic, sensed heart rates (i.e. paced or sensed atrial rates). For example, the HS signal acquisition protocol may involve verifying two or more different heart rates over a monitoring period of time, e.g. a 24-hour period, a one week period, etc., to enable HS signal data to be acquired for multiple heart rates. If the patient is being paced by a rate-responsive pacemaker, HS signal data may be acquired over a period of time at different sensor-indicated pacing rates. In some embodiments, HS signals are acquired for a fixed AV or W interval during multiple heart rates to determine a trend of a HS parameter as a function of heart rate.

As such, a physiological control condition is verified at block 1004 using another sensor signal, which may be, but is not limited to, an EGM or ECG signal, an activity signal, or a posture signal. Once an initial control condition, such as a heart rate, activity level or patient posture or any combination thereof, is verified, the pacing protocol is initiated at block 1006. As mentioned above, the pacing protocol may include a single pacing parameter setting applied during multiple physiological control conditions, such as a single AV interval, single VV interval, or single LV pacing site. In other embodiments, multiple settings of one or more pace control parameters are applied during the pacing protocol as described previously.

At block 1008, HS signals are acquired for the verified control condition and an initial setting for a pace control parameter. One or more HS signal parameters are determined at block 1010. The protocol advances to the next pace control parameter setting at block 1014 until all pace control parameter settings to be tested have been applied, as determined at block 1012. It is contemplated that the verified control condition may be monitored during HS signal acquisition at multiple pace control parameter settings to ensure that the condition remains substantially stable for each of the pace parameter settings.

Once all settings have been applied, which may be as few as one, the process determines if additional control conditions remain to be tested at block 1016. If so, the process returns to block 1004 and waits until the next physiological condition is detected and verified. For example, a cardiac electrical signal may be monitored until a different intrinsic heart rate is detected. In some embodiments, a pacing rate may be adjusted to induce a different heart rate. A change from a supine posture to an upright posture (or vice versa) may be verified and/or a change in activity level may be verified in or to begin collecting HS data during the pacing protocol at the next control condition.

Once HS data is collected for multiple pace control parameter settings during two or more physiological control conditions, as determined at block 1016, the trend of each HS parameter as a function of the pace parameter is determined for each control condition at block 1018. If only a single pace control parameter was tested for each physiological control condition, a trend of the HS signal parameter(s) with respect to the changes in the control condition is determined at block 1018.

The patient's HS response profile is established as the trends of each HS parameter with respect to pace parameter setting and/or control condition. The HS profile is compared to previously established matching criteria at block 1020 for classifying the profile according to population-based classifications at block 1022. Different HS parameter trends at different heart rates, different patient posture, or other control conditions may correlate to different responses to CRT or other heart failure therapies. As such, determining the HS parameter trend with respect to different physiological control conditions, in combination with varying pace control parameters or for fixed pace control parameters, can provide useful data for classifying a patient as a "responder", "non-responder" or other therapy response classifications.

It is further contemplated that a HS response profile may include a HS parameter trend over different control conditions using a fixed pace control parameter settings and a HS parameter trend over varying pace control parameter settings for a single control condition. For example, a HS response profile may include determining a HS parameter trend over multiple heart rates during pacing using a fixed AV interval and a HS parameter trend over multiple AV interval settings applied during a single heart rate.

Thus, a medical device system and associated method have been presented in the foregoing description with reference to specific embodiments. It is appreciated that various modifications to the referenced embodiments may be made without departing from the scope of the disclosure as set forth in the following claims.

The invention claimed is:

1. A medical device system, comprising:
  a plurality of electrodes for delivering cardiac pacing pulses to a patient's heart;
  a cardiac sensing module coupled to the plurality of electrodes;
  a cardiac pacing module coupled to the plurality of electrodes for generating cardiac pacing pulses;
  an acoustical sensor for obtaining heart sound signals;
  a processor configured to establish a plurality of conditions for acquiring heart sound signals, receive the heart sound signals during each of the plurality of established conditions, derive a plurality of heart sound signal parameters from the heart sound signals, and determine a heart sound response profile comprising a trend of each of the plurality of heart sound signal parameters with respect to the plurality of established conditions; and
  a memory storing a plurality of profile classification definitions, wherein the processor is further configured to determine a closest match between one of the plurality of profile classification definitions and the heart sound profile, and provide a classification of the heart sound profile according to the closest matching profile classification.

2. The system of claim 1, further comprising a physiological sensor, wherein establishing the plurality of conditions by the processor comprises verifying a physiological condition in response to a signal received from the physiological sensor.

3. The system of claim 1, wherein establishing the plurality of conditions by the processor comprises controlling the cardiac pacing module to deliver the cardiac pacing pulses at a plurality of pace parameter settings.

4. The system of claim 1, further comprising an external processing device configured to receive heart sound profiles for a plurality of patients and receive reference measurements for the plurality of patients, the external processing device configured to group the plurality of patients into a plurality of groups according to the reference measurements, and define heart sound profile matching criteria for each of the plurality of groups based on the heart sound profiles for the plurality of patients.

5. The system of claim 1, wherein the heart sound parameters comprise a time interval from a reference point to a second heart sound.

6. The system of claim 5, wherein the reference point comprises one of a first heart sound, a ventricular pacing pulse, and a ventricular sensed R-wave.

7. The system of claim 1, wherein the processor is further configured to predict a response to a cardiac therapy in response to the heart sound profile.

8. The system of claim 7, wherein the processor is further configured to recommend whether a pace parameter setting be adjusted during the cardiac therapy in response to the predicted response.

9. The system of claim 8, wherein the processor is configured to recommend optimization of an atrial-ventricular pacing interval in response to determining a heart sound profile comprising a sudden change in a trend of the time interval.

10. The system of claim 1, wherein determining the heart sound profile comprises determining a trend of a first heart sound amplitude with varying atrial-ventricular pacing interval.

11. The system of claim 1, further comprising a display of the heart sound profile.

12. A method for use in a medical device system for predicting a patient response to a therapy, the method comprising:
  establishing a plurality of conditions for acquiring heart sound signals;
  obtaining heart sound signals from an acoustical sensor during each of the plurality of conditions;
  deriving a plurality of heart sound signal parameters from the heart sound signals, and determining a heart sound profile comprising a trend of each of the plurality of heart sound signal parameters with respect to the plurality of conditions;
  storing a plurality of profile classification definitions in a memory of the medical device system;
  determining a closest match between one of the plurality of profile classification definitions and the heart sound profile; and
  classifying the heart sound profile according to the closest matching profile classification.

13. The method of claim 12, wherein establishing the plurality of conditions comprises verifying a physiological condition in response to a signal received from a physiological sensor.

14. The method of claim 12, wherein establishing the plurality of conditions comprises controlling a cardiac pacing module to deliver cardiac pacing pulses at a plurality of pace parameter settings.

15. The method of claim 12, further comprising:
  receiving heart sound profiles and reference measurements for a plurality of patients;
  grouping the plurality of patients into a plurality of groups in response to the reference measurements; and
  defining heart sound profile matching criteria for each of the plurality of groups based on the heart sound profiles for the plurality of patients.

16. The method of claim 12, wherein deriving the heart sound parameters comprises deriving a time interval from a reference point to a second heart sound.

17. The method of claim 16, wherein the reference point comprises one of a first heart sound, a ventricular pacing pulse, and a ventricular sensed R-wave.

18. The method of claim 12, further comprising determining a response to a cardiac therapy in response to the heart sound profile.

19. The method of claim 18, further comprising recommending whether the pace parameter setting be adjusted during the cardiac therapy in response to the determined response.

20. The method of claim 19, further comprising recommending optimization of an atrial-ventricular pacing interval during the cardiac therapy in response to determining a heart sound profile comprising a sudden change in a trend of the time interval.

21. The method of claim 12, wherein determining the heart sound profile comprises determining a trend of a first heart sound amplitude with varying atrial-ventricular pacing interval.

22. The method of claim 12, further comprising generating a display of the heart sound profile.

23. A non-transitory computer-readable medium storing instructions which cause a medical device system to perform a method comprising:
   establishing a plurality of conditions;
   obtaining heart sound signals from an acoustical sensor during each of the plurality of conditions;
   deriving a plurality of heart sound signal parameters from the heart sound signals, and determining a heart sound profile comprising a trend of each of the plurality of heart sound signal parameters with respect to the plurality of conditions;
   storing a plurality of profile classification definitions in a memory of the medical device system;
   determining a closest match between one of the plurality of profile classification definitions and the heart sound profile; and
   classifying the heart sound profile according to the closest matching profile classification.

* * * * *